United States Patent [19]

Fotheringham et al.

[11] Patent Number: 5,354,672
[45] Date of Patent: Oct. 11, 1994

[54] MATERIALS AND METHODS FOR HYPERSECRETION OF AMINO ACIDS

[76] Inventors: Ian Fotheringham, 10 Southfield Dr., Vernon Hills, Ill. 60061; Jennifer Ton, 950 Countryside Dr. #219, Palatine, Ill. 60067; Chris Higgins, Pipal Cottage, Water Eaton, OX28HE, Oxford, England

[21] Appl. No.: 985,694

[22] Filed: Nov. 24, 1992

[51] Int. Cl.⁵ .................. C12P 13/04; C12N 1/21; C12N 15/09
[52] U.S. Cl. .................. 435/106; 435/108; 435/113; 435/172.3; 435/252.3; 435/252.33; 435/370.1; 935/72; 935/73; 536/23.7; 536/23.72
[58] Field of Search .......... 435/252.3, 252.33, 172.3, 435/320.1, 106, 108, 113; 935/72, 73; 536/23.7, 23.72

[56] References Cited

PUBLICATIONS

H. E. Huber et al. "Expression of Bacteriophage P in Recombinase . . ." Gene 34:63–72 (1985).
R. H. A. Plastenk et al. "A Genetic Switch in Vitro: DNA inversion . . . " Proc. Natl. Acad. Sci. 81:2689–2692 (May 1984).
K. Kutsukake et al. "A Gene for DNA invertase and an . . . " Gene 34: 343–350 (1985).
Birnboim, H. C. and Doly, J., *Nucleic Acids Res.* 7:1513–1523 (1979).
Hashimoto-Gotoh, *Gene* 16:227–235 (1981).
Nelms, *App. Environ. Microbol* 58:2592–2598 (1992).
Roberts, et al., *Studies of Biosynthesis in E. coli*, pp. 4–5 (Carnegie Inst. 1955).
Stoker, et al. *Gene* 18:355–341 (1982).

*Primary Examiner*—Keith Baker
*Assistant Examiner*—Rebecca Prouty
*Attorney, Agent, or Firm*—Marshall, O'Toole, Gerstein, Murray & Borun

[57] ABSTRACT

Disclosed are novel bacterial cells characterized by hypersecretion of an amino acid, wherein a DNA inversion gene has been incorporated into said bacterial cells. Also disclosed are methods of producing said bacterial cells and methods of producing amino acids from said bacterial cells.

12 Claims, No Drawings

MATERIALS AND METHODS FOR HYPERSECRETION OF AMINO ACIDS

BACKGROUND OF THE INVENTION

The present invention relates generally to methods and materials for active (extracellular) secretion of amino acids which are expression products of bacterial cells.

Hypersecretion of amino acids from bacterial cells is of manifest importance in the large-scale production of amino acids in industrial processes. To date, a means of constructing cells which actively excrete large amounts of an amino acid as compared to wild-type cells is not reported. Previous attempts to increase the extracellular presence of amino acids have centered on decreasing amino acid uptake by introducing mutations in, for example, phenylalanine uptake pathways. However, such techniques produce only marginal net increases in amino acid efflux by decreasing active uptake by the cell of amino acids already lost to the medium by diffusion. For purposes of the present application, hypersecretion refers to the active secretion from host cells of quantities of an amino acid greater than quantities which passively diffuse from corresponding wild-type cells.

There is a need in the art for host cells capable of secreting large amounts of an amino acid as compared to the corresponding wild-type cells in order to facilitate production of the amino acid and to relieve toxic and inhibitory effects of high intracellular levels of amino acids. The present invention provides novel bacterial cells capable of hypersecreting an amino acid.

SUMMARY OF THE INVENTION

The present invention provides novel bacterial cells capable of hypersecreting an amino acid. In a preferred embodiment of the invention, the hypersecreted amino acid is tyrosine, methionine, or phenylalanine and the bacterial cell is an *Escherichia coli* cell.

In a preferred embodiment of the invention, a DNA inversion gene is introduced into a cell which is capable of manufacturing the amino acid of interest. DNA inversion genes, which may alternatively be referred to as invertases, include, inter alia, the cin gene of bacteriophage P1, the gin gene of bacteriophage mu, the hin gene of *Salmonella typhimurium*, and the pin gene of *Escherichia coli*. Any of the invertases may be introduced, via an appropriate prophage or via a vector, directly into a host cell capable of manufacturing an amino acid of interest in order to effect hypersecretion of the amino acid.

In a preferred embodiment of the invention, the invertase gene is introduced into a host cell by incorporation of an appropriate prophage in order to create a lysogen of the target host cell. Most preferably, the cin gene may be incorporated by introducing the P1 prophage into the host cell and the gin gene may be incorporated by introducing the mu prophage into the host cell.

In a preferred embodiment of the invention, any of the invertases may be introduced via an appropriate transformation vector which may preferably be a plasmid with a temperature-sensitive copy number and may most preferably be plasmid pHSG415.

In another aspect of the invention *E. coli* cells capable of hypersecreting phenylalanine are further transformed with a plasmid containing a pheA 34 gene in order to provide even greater levels of phenylalanine export than would occur by transformation with an invertase alone.

In a preferred embodiment of the invention, the invertase is transiently present or transiently active in the host bacterial cell and the bacterial cell is fixed in the hypersecreting mode.

In yet another aspect of the invention, methods of producing bacterial cells capable of hypersecreting an amino acid are disclosed, wherein bacterial cells are transformed or transfected with a prophage or with a vector containing an invertase. The transformed or transfected bacterial cells are then selected and plated on a medium which has been seeded with a strain of *E. coli* incapable of synthesizing the hypersecreted amino acid. Bacterial cells which hypersecrete the amino acid but which no longer contain the vector are then isolated.

In a preferred embodiment of the aforementioned method, the bacterial cells are *Escherichia coli* cells, the hypersecreted amino acid is tyrosine, methionine, or phenylalanine, and the invertase is transiently incorporated into the host cell.

In yet another aspect of the invention, a method of producing an amino acid is presented, wherein bacterial cells capable of hypersecreting an amino acid are fermented in an appropriate medium and the hypersecreted amino acid is then harvested from the medium.

It is also contemplated that the above-described hypersecretor phenotype is induced by incorporation of members of the resolvase family into a bacterial cell in a manner essentially similar to that described for the invertases. The resolvases include Tn3, gamma delta, TN501, Tn21, and Tn1721. The resolvase genes are derived from the Tn3 family of transposons and bear substantial sequence homology to members of the invertase family. Incorporation of a resolvase, or a vector comprising a resolvase, into a bacterial cell also results in hypersecretion of one or more amino acids.

Numerous additional aspects and advantages of the invention will be apparent to those skilled in the art upon consideration of the following detailed description of the invention.

DETAILED DESCRIPTION OF THE INVENTION

The following detailed description relates to the production and use of bacterial cells capable of hypersecreting amino acids. Such cells are the result of transformation or transfection with an invertase or transformation or transfection with an invertase and with a pheA 34 gene in an appropriate vector. Cells in which an invertase has been incorporated generally display a 1% rate of reversion to the wild-type secretion pattern, as well as a 1% re-reversion rate (i.e., to the hypersecretor mode). In order to compensate for the aforementioned reversion to the wild-type secretion rate and to "lock" target bacterial cells in the hypersecretor mode, the invertase may be transiently introduced into bacterial cells and any cells which are in the hypersecretor mode upon removal or inactivation of the invertase may be selected as cells according to the present invention.

Example 1 provides means of incorporating a P1 prophage into a host bacterial cell. Example 2 reports results demonstrating that lysogens produced in Example 1 hypersecrete amino acids. Example 3 relates to the incorporation of an invertase into a plasmid vector.

Example 4 provides means of incorporating plasmids containing an invertase into a bacterial cell and results of an examination to confirm the presence of the hypersecretor phenotype. Example 5 relates to stabilization of the phenotype and Example 6 provides additional confirmation of the hypersecretor phenotype in the form of quantitative data.

EXAMPLE 1

The various DNA inversion genes (invertases) described above are responsible for switching on expression of the hypersecretor phenotype. By way of illustration, a P1 prophage which contains the cin gene of bacteriophage P1 was directly incorporated into an *E. coli* cell. It is readily apparent to the skilled artisan that other invertases may be incorporated into a bacterial cell using similar procedures and that the P1 prophage is used herein for exemplification.

A strain of bacteriophage P1, P1 cml clr, was used for transfection into an *E. coli* cell. A source of the cml clr strain of P1 is *E. coli* strain CSH128 which is disclosed in *A Short Course in Bacterial Genetics Strain Kit*, which is available from the Cold Spring Harbor Laboratory Press as a companion to Miller, *A Short Course in Bacterial Genetics* (Cold Spring Harbor Laboratory Press, 1992). That strain of P1 generates lysogens in a temperature-sensitive fashion, with temperatures of about 30°–35° C. being most conducive to lysogen formation. The P1 prophage was prepared from a lysogenic strain of *E. coli* designated HW1107 for incorporation into the *E. coli* test strain, HW1089 (ATCC Accession No. 55371). However, any *E. coli* strain which is lysogenic for P1 cml clr may be used for preparation of a P1 prophage. The HW1107 cells were grown with aeration in 25 mls of LB broth medium (GIBCO/BRL, Paisley, Scotland) at 32° C. until they reached a density of $2 \times 10^8$ cells/ml. The cells were then further grown for 90 minutes at 40° C. The culture was then spun at 10,000 rpm for 10 minutes to remove the cells. A 1 ml aliquot of the supernatant containing the P1 prophage in suspension was removed and placed in a sterile 1.5 ml polypropylene tube to which was added 10 μl chloroform. The suspension was stored at 4° C.

Suspensions containing the P1 prophage were then incubated with HW1089 cells which had been grown with aeration in 25 mls of LB broth medium containing 2.5 mM $CaCl_2$ at 37° C. until the culture density reached $2 \times 10^8$ cells/ml. A volume of 100 μl of HW1089 cells was then removed and combined in a 10 ml polypropylene tube with 2 μl of the P1 phage suspension described above. The mixture was incubated without shaking for 20 minutes in a 37° C. water bath and spread on LB agar plates containing 10 μg/ml chloramphenicol. The P1 prophage contains a chloramphenicol resistance marker. Following overnight incubation at 32° C., lysogens were isolated as chloramphenicol resistant colonies and examined for the ability to hypersecrete phenylalanine and tyrosine as described in Example 2.

EXAMPLE 2

Lysogens of HW1089 as described above were selected on LB agar plates containing kanamycin. Colonies were pooled and plated on cross-feeding agar plates containing M9 minimal salts medium (Roberts, et al. *Studies of Biosynthesis* in *E. coli*, page 607 (Carnegie Inst. 1955)) supplemented with 0.2% glucose, 100 μM $CaCl_2$, 1 mM $MgSO_4$, and 5 μg/ml Vitamin B1. These plates also contained approximately $10^7$ cells/ml of either *E. coli* strain HW1012 or *E. coli* strain HW1011. The former strain possesses a mutation which makes supplementation with phenylalanine necessary for growth and the latter strain possesses a mutation which makes supplementation with tyrosine and phenylalanine necessary for growth. These strains are used herein for the purpose of exemplification. The skilled artisan recognizes that numerous phenylalanine and tyrosine auxotrophs may be used in cross-feeding experiments in the manner described for HW1011 and HW1012.

The existence of HW1089 lysogens which hypersecrete phenylalanine was determined by the presence of halos caused by growth of HW1012 cells surrounding the HW1089 colonies and the existence of HW1089 lysogens which hypersecrete tyrosine and phenylalanine was determined by halos of HW1011 cells. The presence of such halos indicated that HW1012 or HW1011 cells grew because they utilized the phenylalanine or tyrosine which was hypersecreted from HW1089 lysogens.

Wild-type (i.e., non-transformed) HW1089 cells do not secrete sufficient amounts of phenylalanine or tyrosine to support more than very limited growth of surrounding HW1012 or HW1011 cells, respectively.

The HW1089 lysogens were plated at a dilution which gave rise to approximately 100 colonies per plate. Halos of HW1011 and HW1012 cells were clearly visible surrounding the HW1089 lysogens, indicating that the lysogens were hypersecreting phenylalanine and tyrosine. Example 3 demonstrates that same phenomenon wherein the invertase is introduced into *E. coli* via a transformation vector.

EXAMPLE 3

The cin gene of bacteriophage P1 was next incorporated into a plasmid vector for use in the transformation of bacterial cells. Induction of hypersecretion is exemplified herein by reporting results obtained using the cin gene to induce phenylalanine and tyrosine hypersecretion. However, the skilled artisan readily recognizes that any of the family of invertases described above will function similarly to induce hypersecretion of phenylalanine, tyrosine, and methionine in an appropriate bacterial cell.

The multi-copy plasmid vector, PLG338 was used as a vehicle for the introduction of the cin gene into *E. coli* test strains. Plasmid PLG338 is fully described in Stoker, et al., Gene, 18:355-341 (1982), the disclosures of which are incorporated herein by reference. In order to produce copies of the cin gene for incorporation into PLG338, DNA comprising the cin gene was PCR amplified from bacteriophage P1 using the primers:
MB1176, 5' CCGGAATTCGAGCATTATTGT-GAAATCAC 3' (Seq. ID No. 1) and
MB1177, 5' CGCGGATCCCGAGTTCTCT-TAAACCAAGGTTTA 3' (Seq. ID No 2).
The amplified cin gene DNA, the nucleotide sequence of which is set forth in Seq. ID No. 3, comprised the coding and promoter regions of the gene. Amplification with PCR was accomplished using a 0.2 ml MicroAmp ™ reaction tube (Perkin-Elmer, Norwalk, Conn.) to which was added 100 ng P1 DNA (1 μl); 5 μl of each primer at a concentration of 10 ng/ml; 2 μl each of dATP, dGTP, dCTP, dTTP (10 mM each); 10 μl of buffer comprising 15 mM $MgCl_2$, 500 mM $KCl_2$, 100 mM Tris (PH 8.3), and 0.01% gelatin; a taq DNA polymerase (0.5 μl at 5u/μl, Amplitaq ™ ); and distilled water to a total volume of 100 μl. The tube was capped and placed in a Perkin Elmer 9600 TM PCR Thermal Cycler (Perkin-Elmer). Amplification was carried out by pre-heating at 94° C. for 3 minutes, followed by 25 cycles of Denaturation at 94° C. for 30 seconds, annealing at 50° C. for 30 seconds, and extension at 72° C. for 1 minute. The reaction mixture was then stored at 4° C.

Approximately 1 μg of the PCR amplified fragment was digested with the restriction enzymes EcoRI and BamHI to generate sticky ends at unique EcoRI and BamHI sites within the primer sequences. Approximately 1 μg of plasmid pLG338 was also cleaved at unique EcoRI and BamHI sites. The larger (approximately 7.1kb) plasmid fragment was then isolated by gel electrophoresis in low melting point agar and recovered using a Prep-A-Gene TM kit (Bio-Rad, Richmond, Calif.) according to the manufacturer's instructions. The PCR amplified fragment was then ligated to the plasmid fragment in a 20 μl ligation mixture comprising 50 mM Tris pH 7.8, 10 mM MgCl$_2$, 20 mM DTT, 1 mM ATP, 50 mg/ml BSA, and 400 units of DNA ligase (New England BioLabs, Beverly, Mass.). The resulting plasmid, designated PIF906, was introduced into *E. coli* cells which were then examined for display of the hypersecretor phenotype as taught in Example 4.

EXAMPLE 4

Bacterial cells which produce the amino acid to be hypersecreted are preferred host cells of the present invention. A particular bacterial cell strain, namely *E. coli* strain HW1089, was used to demonstrate hypersecretion of phenylalanine and tyrosine. However, it is apparent to one of ordinary skill in the art that other suitable bacterial cells may be used and that amino acids other than phenylalanine and tyrosine, especially methionine, may be hypersecreted by application of the present methods.

Plasmid PIF906, as constructed above, was introduced into *E. coli* strain HW87 by electroporation using a Bio-Rad Gene Pulser TM set to 2.5 kv with 25 μF capacitance and a Bio-Rad pulse controller set to 200 ohms resistance. Cells were carried in Bio-Rad Gene Pulser TM cuvettes with a 0.2 cm gap. Strain HW87 is fully described in Nelms, *App. Environ. Microbiol*, 58:2592-2598 (1992), the disclosures of which are incorporated herein by reference.

*Escherichia coli* cells to be transformed were grown to an optical density of 0.7 at 600 nm. The cells were then recovered by centrifugation at 10,000 g for 5 minutes and then washed in 30 ml deionized distilled water. The cells were re-spun and re-suspended in 200 μl deionized distilled water and 40 μl of cells were mixed with 2 μl of the ligation mixture described above and 8 μl deionized distilled water and placed in an electroporation cuvette. A single pulse was applied to the cuvette and 500 μl SOC medium (GIBCO/BRL, Gaithersburg, Mo.) was added and mixed with the cell suspension. The contents of the cuvette were then transferred to a 20 ml pvc tube and incubated for 30 minutes at 30° C. The cells were then plated on appropriate media as described below. Additional transformation procedures are known and available to those skilled in the art.

Positive transformants were selected by plating the HW87 cells on LB agar medium (GIBCO/BRL, Paisley, Scotland) containing 40 μg/ml of the antibiotic kanamycin (Sigma, St. Louis, Mo.). This enables selection of positive transformants due to the presence of a kanamycin resistance locus in the plasmid.

All positive transformants were pooled in order to increase the likelihood of identifying correctly synthesized PCR product and the plasmid DNA was isolated according to the procedure described in Birnboim, H.C. and Doly, J., *Nucleic Acids Res*, 7:1513-1523 (1979). Isolated pooled plasmid DNA was then used to separately transform cells of *E. coli* strain HW1089 (ATCC Accession No. 55371) by the electroporation technique described above. Strain HW1089 displays a deficiency in phenylalanine and tyrosine uptake. Because of these deficiencies, strain HW1089 recaptures less of any secreted phenylalanine and tyrosine, respectively, than would their wild-type counterparts.

Positive transformants of HW1089 were again selected on LB agar plates containing kanamycin. Colonies were pooled and plated on cross-feeding agar plates containing M9 minimal salts medium (Roberts, et al. *Studies of Biosynthesis* in *E. coli*, page 607 (Carnegie Inst. 1955)) supplemented with 0.2% glucose, 100 μM CaCl$_2$, 1 mM MgSO$_4$, and 5 μg/ml Vitamin B1. These plates also contained approximately $10^7$ cells/ml of either *E. coli* strain HW1012 or *E. coli* strain HW1011. As previously mentioned, the former strain possesses a mutation which makes supplementation with phenylalanine necessary for growth and the latter strain possesses a mutation which makes supplementation with tyrosine and phenylalanine necessary for growth. Other suitable phenylalanine and/or tyrosine auxotrophs may also be used as cross-feeding cells.

The existence of HW1089 cells which hypersecrete phenylalanine was determined by the presence of halos caused by growth of HW1012 cells surrounding the HW1089 colonies and the existence of HW1089 cells which hypersecrete tyrosine and phenylalanine was determined by halos of HW1011 cells. The presence of such halos indicated that HW1012 or HW1011 cells grew because they utilized the phenylalanine and/or tyrosine which was hypersecreted from HW1089 cells.

Wild-type (i.e., non-transformed) HW1089 cells do not secrete sufficient amounts of phenylalanine or tyrosine to support more than very limited growth of surrounding HW1012 or HW1011 cells, respectively.

The transformed HW1089 cells were plated at a dilution which gave rise to approximately 100 colonies per plate. Colonies of HW1089 cells which were identified as hypersecreting phenylalanine were again purified on M9 minimal medium plates without HW1012 or HW1011 cells and were re-tested on cross-feeding plates as described above. Although these cells continued to secrete elevated levels of phenylalanine, about 1% of the cells consistently reverted to the wild-type phenotype. Of that 1%, approximately 1% subsequently reverted back to the hypersecretor phenotype. This 1% reversion rate was the same as that observed for the aforementioned switching mechanism controlled by the cin gene in the P1 prophage. This indicated that the cloned cin gene was responsible for switching the hypersecretor gene on (and off again in the case of reversions), possibly by causing rearrangement of DNA encoding the hypersecretor phenotype.

Having successfully constructed hypersecreting cells and having identified the mechanism by which the hypersecretor phenotype is switched on, it was desirable to stabilize the phenotype as taught in Example 5 in order to prevent reversion to the wild-type secretion pattern.

EXAMPLE 5

Transient introduction of an invertase into HW1089, wherein the invertase is removed when the cell is in the hypersecretor mode, is one means of stabilizing transformed cells in the hypersecretor mode and doing so eliminates the 1% reversion described above. The same effect may be obtained by inactivation of the invertase.

Transient introduction of the cin gene was achieved using a derivative of plasmid pSC101. The derivative, plasmid HSG415 (Hashimoto-Gotoh, Gene, 16: 227–235 (1981)), is only stable in *E. coli* cells at temperatures of 34° C. or lower. As the temperature rises above 34° C., HSG415 is unable to replicate and is lost as the host cells divide. By transforming HW1089 cells with plasmid HSG415 bearing the cin gene, identifying the hypersecretors, and raising the temperature beyond 34° C., at least some of the progeny of the original HW1089 cells will be fixed in the hypersecreting mode.

To do this, the cin gene was introduced into plasmid HSG415 in the manner described above for introduction of the cin gene into plasmid pLG338. The method of cloning the cin gene into HSG415 was almost identical to that described for the cloning of cin into pLG338. Plasmid HSG415 was cleaved with EcoR1 and BamHI at unique sites within the plasmid. The largest (approximately 4.8 Kb) fragment produced from HSG415 was isolated and ligated to a cin fragment which had also been cleaved at unique EcoR1 and BamHI sites. The ligation of the cin fragment to the HSG415 fragment and introduction of the resulting product into *E. coli* was accomplished as described above for pIF906. The resulting construction was designated pIF907. Positive transformants were identified on LB agar plates containing ampicillin at 100 µg/ml as HSG415 contains an ampicillin resistance marker. Surviving colonies were pooled and the plasmid DNA was isolated and used to transform HW1089 cells as described above. These transformants were again pooled and plated on HW1012 and HW1011 cross-feeder plates as described above. The plates were incubated at 32° C. Approximately 30% of the colonies were identified as cross-feeding by the presence of halos of cross-fed (HW1012 or HW1011) cells.

Of those colonies identified as cross-feeding, one colony was selected and purified on a fresh cross-feeding plate. That colony exhibited almost complete stability of the hypersecretor phenotype. This was unexpected because the colony had been grown at a permissive temperature (32° C.). However, by plating cells from the selected colony on separate LB plates it was determined that the plasmid had already disappeared from the cells (i.e., the cells no longer displayed ampicillin resistance). This was attributed to the fact that, even at lower temperatures, the plasmid is unstable and the host cells do not readily tolerate multiple copies of the cin gene. Thus, not having maintained its replication at the same rate as the host cell, the plasmid was lost from certain cells which happened to be in the hypersecretor mode. By virtue of losing the plasmid, these cells became fixed in the hypersecretor mode. These "fixed" hypersecretor cells were then tested to quantitate their phenylalanine output and the results are shown in Example 6.

EXAMPLE 6

The HW1089 cells which were fixed in the hypersecretor mode as described above were designated CF1. These cells were further purified by streaking twice on LB Agar plates from single colonies. Another derivative of hypersecreting HW1089 cells was also constructed. These cells, designated CF2, were essentially identical to CF1 cells except that they also carried the plasmid pJN307 which bears the pheA 34 allele. That allele causes deregulation of phenylalanine biosynthesis.

A growth study was conducted to compare the phenylalanine output of CF1 and CF2 cells in relation to a control strain of non-transformed HW1089 cells or HW1089 transformed with only pJN307. To do this, each of the test strains (CF1, CF2, HW1089, HW1089 and pJN307) was streaked on MA Agar plates and grown overnight to produce single colonies. Colonies of each test strain were inoculated into a 35 ml culture of MA medium (13.0 g/l $K_2HPO_4$, 2.0 g/l $KH_2PO_4$, 1.0 g/l $MgSO_4.7H_2O$, 4.0 g/l $(NH_4)_2HPO_4$, 0.24 g/l ferric ammonium citrate, 0.1 g/l yeast extract, and 35 g/l glucose) in a 1 L shake flask and grown at 32° C. in a shaking incubator. Samples containing 1 ml of culture were taken for phenylalanine analysis at 24 and 48 hours. Each 1 ml sample was diluted to 10 mls in water and autoclaved for 5 minutes to completely lyse all cells. The lysate was then filtered through a 0.2 µm filter and collected. The presence of phenylalanine was detected in 1 ml samples of the filtrate by ion-pairing reverse phase HPLC. A 10 µl aliquot of the prepared broth sample was injected by an autosampler onto a Whatman partisil 5 ODS-3 2.1 mm ×10 cm column. The mobile phase consisted of 94% water, 5% acetonitrile and 1% PIC-B5 ion-pairing reagent. The flow rate was 1.5 ml/min. with UV detection carried out at 214 nm. Run time for the samples was 10 minutes, with L-phenylalanine eluting at about 6 minutes. The phenylalanine peak area was measured and the concentration of phenylalanine was determined by comparison with the peak of a prepared L-phenylalanine standard. Duplicate cultures were assayed for each strain.

All samples showed undetectable levels of phenylalanine except CF2 which showed 0.459 and 0.175 g/l (two separate experiments) and one sample of HW1089+pJN307 which showed 0.027 g/l. These results demonstrate that the difference in phenylalanine export between CF2 and HW1089+pJN307 was about 7–15 fold. As expected, incorporation of the pheA 34 gene further enhanced phenylalanine production in CF2 cells due to the increased phenylalanine synthesis caused by that gene. The results are shown in Table 1 below. CF1 cells into which pJN307 was introduced are designated CF2.

TABLE 1

| HOST CELL STRAINS | PHENYLALANINE OUTPUT |
| --- | --- |
| Control HW1089 | Undetectable |
| CF1 | Undetectable |
| CF2 | 0.45 g/l and 0.175 g/l |
| Control HW1089 + PJN307 | undetectable and 0.027 g/l |

As shown in Table 1, the introduction of pJN307 increased hypersecretion in CF2 cells. Due to the sensitivity limits of the assay, only CF2 cells exhibited detectable levels of phenylalanine output. However, CF1 cells were previously confirmed to hypersecrete phenylalanine by the more sensitive cross-feeding assay described above.

Therefore, both CF1 cells alone and CF2 cells exported greater amounts of phenylalanine than wild-type control cells. As is clear to the skilled artisan, cells may be transformed to secrete other amino acids by introduction of the cin gene as taught herein. Thus, the example demonstrating phenylalanine hypersecretion is provided herein for the purposes of illustrating a preferred embodiment of the invention which is only limited by the scope of the appended claims.

We claim:

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

| | |
|---|---:|
| CCGGAATTCG AGCATTATTG TGAAATCAC | 2 9 |

( 2 ) INFORMATION FOR SEQ ID NO:2:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

| | |
|---|---:|
| CGCGGATCCC GAGTTCTCTT AAACCAAGGT TTA | 3 3 |

( 2 ) INFORMATION FOR SEQ ID NO:3:

( i ) SEQUENCE CHARACTERISTICS:
( A ) LENGTH: 751 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

| | | | | | | |
|---|---|---|---|---|---|---:|
| CCGGAATTCG | AGCATTATTG | TGAAATCACA | CATAACTATT | TCCTTAATAG | TGAATTAAAT | 6 0 |
| ATCATTGGGA | AACGGTATGT | ACTTTGTGAT | TTCCACACAT | ACTGGTTTTT | GTTAATTAAA | 1 2 0 |
| ATCCGCAGCT | TGCTATAAAT | AACGATAGTG | AGCAGAAAAT | ATGCTAATAG | GCTATGTACG | 1 8 0 |
| CGTATCAACA | AATGAACAAA | ACACTGCTTT | ACAACGAAAC | GCTCTTGAAA | GCGCAGGATG | 2 4 0 |
| TGAGCTAATT | TTTGAGGACA | AGGCGAGCGG | CAAAAAGGCT | GAGCGCCTG | GGTTAAAAAA | 3 0 0 |
| GGTACTCCGT | ATGCTTTCCA | GAGGTGATAC | CCTAGTCGTA | TGGAAGTTAG | ACCGTCTTGG | 3 6 0 |
| GCGCAGCATG | CGTCACTTAG | TTGTGCTGGT | GGAAGAGCTG | CGTGACAGAG | GCATTAACTT | 4 2 0 |
| CCGGAGTCTC | ACTGACTCCA | TCGACACCAG | TACACCAATG | GGGCGCTTTT | TCTTTCACGT | 4 8 0 |
| AATGGGGGCG | CTGGCAGAAA | TGGAACGTGA | GCTTATCGTT | GAACGTACAC | GCGCTGGACT | 5 4 0 |
| TGATGCAGCT | CGCGCAGAAG | GTCGTATAGG | TGGGCGTCGG | CCTAAATACC | AAGAAGAAAC | 6 0 0 |
| ATGGCAGCAA | ATGCGGCGAT | TGCTGGAGAA | GGGCATCCCC | CGTAAGCAGG | TTGCAATCAT | 6 6 0 |
| CTATGATGTG | GCTGTTTCCA | CGCTTTATAA | GAAGTTTCCG | GCGTCATCAT | TTCAATCCTA | 7 2 0 |
| AACCTTGGTT | TAAGAGAACT | CGGGATCCGC | G | | | 7 5 1 |

1. A biologically pure culture of *Escherichia coli* cells comprising a DNA inversion gene, wherein said *Escherichia coli* cells exhibit stable hypersecretion of an amino acid.

2. The *Escherichia coli* cells as recited in claim 1, wherein said cells are transformed or transfected with a vector comprising a DNA inversion gene.

3. The *Escherichia coli* cells as recited in claim 2, wherein said vector is a plasmid with a temperature-sensitive copy number.

4. The *Escherichia coli* cells as recited in claims 1, 2, or 3, wherein the *Escherichia coli* cells are further transformed or transfected with a vector containing a pheA 34 gene.

5. The *Escherichia coli* cells as recited in claim 4, wherein said amino acid is selected from the group consisting of phenylalanine, tyrosine, and methionine.

6. The Escherichia coli cell as recited in claim 4, wherein the DNA inversion gene is selected from the group consisting of the cin gene of bacteriophage P1, the gin gene of bacteriophage mu, the bin gene of *Salmonella typhimurium*, and the pin gene of *Escherichia coli*.

7. The *Escherichia coli* cells as recited in claim 4, wherein the DNA inversion gene is transiently active in the cells.

8. A method of producing *Escherichia coli* cells having a phenotype comprising the stable hypersecretion of an amino acid, said method comprising the steps of:
    transforming or transfecting said *Escherichia coli* cells with a vector containing a DNA inversion gene;
    plating transformed or transfected *Escherichia coli* cells on a plate seeded with a strain of *Escherichia coli* incapable of synthesizing the hypersecreted amino acid; and
    isolating cells which hypersecrete the amino acid and which no longer contain said vector.

9. The method as recited in claim 8, wherein said hypersecreted amino acid is selected from the group consisting of phenylalanine, tyrosine, and methionine.

10. The method as recited in claim 8, wherein said DNA inversion gene is selected from the group consisting of the cin gene of bacteriophage P1, the gin gene of bacteriophage mu, the bin gene of *Salmonella typhimurium*, and the pin gene of *Escherichia coli*.

11. The method as recited in claim 8, wherein said cells which hypersecrete an amino acid and which no longer contain said vector are further transformed with a vector comprising the pheA 34 gene.

12. A method for producing an amino acid comprising the steps of:
    fermenting the *Escherichia coli* cells of claim 4 in an appropriate medium; and
    harvesting the hypersecreted amino acid from the medium.

* * * * *